United States Patent [19]

Scholl

[11] Patent Number: 5,128,471
[45] Date of Patent: Jul. 7, 1992

[54] PROCESS FOR THE PRODUCTION OF ORGANIC AMINES, POLYAMINE MIXTURES AND THEIR USE AS HARDENERS FOR POLYMER PRECURSORS

[75] Inventor: Hans J. Scholl, Coloone, Fed. Rep. of Germany

[73] Assignee: Bayer Aktiengesellshaft, Leverkusen Bayerwerk, Fed. Rep. of Germany

[21] Appl. No.: 507,701

[22] Filed: Apr. 10, 1990

[30] Foreign Application Priority Data

Apr. 14, 1989 [DE] Fed. Rep. of Germany ....... 3912266
Dec. 1, 1989 [DE] Fed. Rep. of Germany ....... 3939699

[51] Int. Cl.$^5$ .................. C07D 401/14; C07D 251/30; C07D 209/62; C07C 209/00
[52] U.S. Cl. ........................................ 544/222; 564/1; 564/215; 564/461; 564/462; 564/488; 564/511; 564/468
[58] Field of Search ................... 564/1, 215, 461, 462, 564/488, 511, 468; 544/222

[56] References Cited

U.S. PATENT DOCUMENTS

| | | | |
|---|---|---|---|
| 3,385,829 | 5/1968 | Heydkamp et al. | 260/75 |
| 3,591,639 | 7/1971 | Tiefenthal et al. | 564/488 |
| 3,766,181 | 10/1973 | Pregler | 544/222 |
| 4,125,724 | 11/1978 | Howell | 564/215 |
| 4,386,218 | 5/1983 | Rasshofer et al. | 564/38 |
| 4,418,160 | 11/1983 | Rasshofer et al. | 521/159 |
| 4,843,107 | 6/1989 | Ruckes et al. | 521/155 |
| 4,843,108 | 6/1989 | Ruckes et al. | 521/155 |

FOREIGN PATENT DOCUMENTS 0128980 12/1977 Fed. Rep. of Germany .
2378748 1/1978 France .
50/70314 6/1975 Japan ................................... 564/215

OTHER PUBLICATIONS

CA 110:38632k.
Chemical Abstracts, vol. 78, No. 23, Jun. 11, 1973, Abstract No. 148005m.
Chemical Abstracts, vol. 80, No. 4, Jan. 28, 1974, Abstract No. 15808v.
Synthesis, 1988, Journal of Synthetic Organic Chemistry, pp. 917-918.

*Primary Examiner*—Carolyn Elmore
*Attorney, Agent, or Firm*—Joseph C. Gil; Thomas W. Roy

[57] ABSTRACT

The present invention relates to a process for the production of primary amines containing aliphatically or cycloaliphatically bound amino groups, characterized in that the isocyanate groups of organic isocyanates containing aliphatically and/or cycloaliphatically bound isocyanate groups are formylated with formic acid in a first reaction step and the N-formyl groups are subsequently converted into amino groups.

The present invention also relates to polyamine mixtures obtained by this process and containing a) about 40 to 90% by weight, based on the total weight of components a) and b), of N,N',N"-tris-(6-aminohexyl)-isocyanurate and b) about 10 to 60% by weight, based on the total weight of components a) and b), of higher homologs of this triamine containing more than one isocyanurate ring.

Finally, the present invention relates to the use of these polyamine mixtures as hardeners for polymer precursors containing epoxide or isocyanate groups.

9 Claims, No Drawings

PROCESS FOR THE PRODUCTION OF ORGANIC AMINES, POLYAMINE MIXTURES AND THEIR USE AS HARDENERS FOR POLYMER PRECURSORS

BACKGROUND OF THE INVENTION

1. Field of the Invention

This invention relates to a new process for the production of organic amines containing aliphatically and/or cycloaliphatically bound primary amino groups, to polyamine mixtures based on N,N',N''-tris-(6-aminohexyl)-isocyanurate and its higher homologs and to the use of these mixtures as hardeners for polymer precursors containing epoxide or isocyanate groups.

2. Description of the Prior Art

The production of primary amines by the hydrolytic decomposition of the isocyanate groups of the corresponding isocyanates is known. Thus, a process for the production of amino-terminated prepolymers from the corresponding NCO prepolymers is described, for example, in EP-A-0 284 887 and EP-A-0 285 948. Both NCO prepolymers contain aliphatically bound isocyanate groups and NCO prepolymers containing aromatically bound isocyanate groups are disclosed as starting materials in these publications, although NCO prepolymers containing aromatically bound isocyanate groups are preferred. In fact, the process according to these prior publications cannot be applied in practice to NCO prepolymers containing aliphatically bound isocyanate groups because unusable product mixtures are formed with poor amine yields as a result of a number of secondary reactions.

Accordingly, it is an object of the present invention to provide a process for the production of organic amines containing a aliphatically bound amine groups from the corresponding organic isocyanates which do not suffer from these defects.

This object has been achieved in accordance with the present invention which relates to a new process for the production of organic amines containing aliphatically and/or cycloaliphatically bound primary amino groups from the corresponding isocyanates. In accordance with this process various primary amines and, in particular, polyamines may be produced in excellent yields. More particularly, the process according to the invention, which is described in detail hereinafter, makes it possible for the first time to produce polyamine mixtures which consist essentially of N,N',N''-tris(6-aminohexyl)-isocyanurate and its higher homologs. These particular polyamine mixtures are particularly valuable hardeners for polymer precursors containing epoxide or isocyanate groups.

SUMMARY OF THE INVENTION

The present invention relates to a process for the production of primary amines containing aliphatically or cycloaliphatically bound amino groups, characterized in that the isocyanate groups of organic isocyanates containing aliphatically and/or cycloaliphatically bound isocyanate groups are formylated with formic acid in a first reaction step and the N-formyl groups are subsequently converted into amino groups.

The present invention also relates to polyamine mixtures obtained by this process and containing a) about 40 to 90% by weight, based on the total weight of components a) and b), of N,N',N''-tris-(6-aminohexyl)-isocyanurate and b) about 10 to 60% by weight, based on the total weight of components a) and b), of higher homologs of this triamine containing more than one isocyanurate ring.

Finally, the present invention relates to the use of these polyamine mixtures as hardeners for polymer precursors containing epoxide or isocyanate groups.

DETAILED DESCRIPTION OF THE INVENTION

Any organic isocyanates containing aliphatically and/or cycloaliphatically bound primary isocyanate groups may be used for the process according to the invention. Suitable organic isocyanates of this type include 1. aliphatic or cycloaliphatic monoisocyanates containing up to 19 carbon atoms such as n-hexyl isocyanate, n-dodecyl isocyanate, n-stearyl isocyanate or cyclohexyl isocyanate;

2. low molecular weight organic polyisocyanates having a maximum molecular weight of 399 such as hyxamethylene diisocyanate, 1-isocyanato-3,3,5-trimethyl-5-isocyanatomethyl cyclohexane or 4,4'-diisocyanatodicyclohexyl methane;

3. relatively high molecular weight organic polyisocyanates containing aliphatically and/or cycloaliphatically bound isocyanate groups and having a molecular weight of at least 400, preferably 400 to about 5,000, such as NCO prepolymers prepared from excess quantities of the diisocyanates defined under 2. and low molecular weight or relatively high molecular weight organic polyhydroxyl compounds which are known from polyurethane chemistry. Especially preferred are prepolymers of the diisocyanates mentioned by way of example and polyether or polyester polyols having a molecular weight above 400, polyisocyanates containing biuret groups such as N,N',N''-tris-(6-isocyanatohexyl)-biuret or mixtures thereof with its higher homologs, and polyisocyanates containing isocyanurate groups and based on the simple diisocyanates mentioned by way of example in 2.

The relatively high molecular weight polyisocyanates mentioned in 3. are preferred over the low molecular weight starting compounds mentioned in 1. and 2. Isocyanurate polyisocyanate mixtures containing a) about 40 to 90% by weight, based on the total weight of components a) and b), of N,N',N''-tris-(6-isocyanatohexyl)-isocyanurate and b) about 10 to 60% by weight, based on the total weight of components a) and b), of higher homologs of this triisocyanate containing more than one isocyanurate ring are particularly preferred for the process according to the invention.

The previously mentioned polyisocyanate mixtures, which are particularly preferred starting materials for the process according to the invention, are formed in known manner by the partial trimerization of the isocyanate groups of hexamethylene diisocyanate with subsequent removal of unreacted starting diisocyanate by distillation. The homolog distribution in the resulting polyisocyanate mixtures depends in particular on the degree of trimerization during the trimerization reaction. The "degree of trimerization" is understood to be the percentage of isocyanate groups in the starting diisocyanate which react during the trimerization reaction. In general, the degree of trimerization in the production of the polyisocyanate mixtures containing isocyanurate groups is about 10 to 40%. A lower degree of trimerization results in a polyisocyanate mixture having a high triisocyanate content, while a high degree of trimerization results in a polyisocyanate mixture having a comparatively greater amount of higher homologs.

Processes for the production of these polyisocyanate mixtures by the partial trimerization of hexamethylene diisocyanate are described, for example, in US-PS 4,324,879, DE-OS 3 100 262 or in Chem. Rev. 72 477 (1972).

In the process according to the invention, at least one equivalent of formic acid is used per NCO equivalent. The quantity is preferably 1 to 1.2 equivalents of formic acid per NCO equivalent.

The reaction with formic acid is generally carried out without a diluent. The formylation reaction may also be carried out in typical NCO-inert diluents, such as hydrocarbons, nitriles and ketones, particularly when the starting isocyanates have a relatively high viscosity, to ensure that the reaction mixture remains stirrable. The progress of the exothermic reaction may be followed by the quantity of $CO_2$ given off (1 mole of $CO_2$ per NCO equivalent). The reaction is generally continued until the evolution of $CO_2$ is complete. At this time all of the NCO groups have been converted into N-formyl groups corresponding to the formula

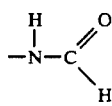

as can be seen from the absence of NCO in the IR spectrum. The formylation reaction is generally carried out at a temperature of about 20° to 150° C., preferably about 40° to 100° C.

The reaction mixture present on completion of the reaction may be worked up, for example, by the removal of low-boiling constituents (e.g., residual formic acid and optionally inert solvents) under vacuum. The distillation residue contains the N-formylated amines or polyamines, which are formed in high yields and in high purity with no significant secondary reactions, as intermediate products of the process according to the invention.

The second stage of the process according to the invention is directed to the conversion of the N-formyl compounds into the end products of the process according to the invention. The second stage of the process according to the invention may be carried out by conventional deformylation reactions known from the literature (cf., for example, T. W. Greene, Protective Groups in Organic Synthesis, John Wiley & Sons, 1981, New York, pages 250/251; S. Patei, The Chemistry of the Amino Group, Interscience Publishers, John Wiley & Sons, 1968, New York, page 671).

Thus, the formyl group may be removal, for example, by hydrolysis with aqueous, organic or inorganic acids. Suitable acids include, in particular, strong acids such as methane sulfonic acid, sulfuric acid and hydrochloric acid. The crude products of the isocyanate/formic acid reaction may advantageously be directly used for this acidic hydrolysis stage. For example, in 1- to 4-normal aqueous hydrochloric acid solutions, the HCl salts of the end products of the process according to the invention are obtained after 1 hour under reflux conditions with subsequent removal of the low-boiling constituents. Aqueous solutions of the free amine mixtures according to the invention (which may be freed from low-boiling constituents, for example by thin-layer distillation) are obtained by neutralization with concentrated alkali hydroxide or with basic ion exchangers.

The conversion of N-formyl groups I into amino groups II can be obtained particularly smoothly and simply by a transformylation reaction in accordance with the following scheme:

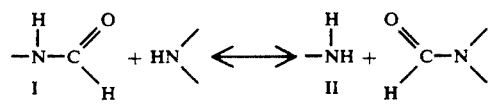

Previously, reactions of this type have merely been generically referred to as "transamidation" reactions for the production of formamides. Thus, monoformylated HDA of poor quality is formed from hexamethylene diamine (HDA) and formamide in the above equilibrium reaction; the reaction has to be carried out at high temperatures and over long reaction times (Synthesis (1988), pages 917–918). Corresponding transamidation reactions are described in EPA 0 271 093 for the production of formamides from amines and dimethyl formamide in the presence of metal oxides as catalysts to shorten the reaction time.

In contrast to the processes described in these publications, the N-formyl groups are replaced by primary amino groups in a smooth reaction in accordance with the present invention without any need for long reaction times, extremely high reaction temperatures or catalysts.

In this transformylation reaction, the N-formylated intermediate products are reacted with primary or secondary amines, the formyl

being replaced by a hydrogen atom.

Amines suitable for this reaction are any primary or secondary amines wherein the amino groups are aliphatically, cycloaliphatically, aromatically or heterocyclically bound. However, it is preferred to use strongly basic amines which have a boiling point at 1013 mbar of about 80° to 150° C., preferably about 90° to 130° C. Suitable and preferred amines are alkyl amines or dialkyl amines containing 3 to 18 carbon atoms such as n-propyl amine, methylethyl amine, n-hexyl amine, n-dodecyl amine or n-stearyl amine; alkylene diamines containing 2 to 6, preferably 2 to 4 carbon atoms, such as ethylene diamine, 1,2- and 1,3-diaminopropane, 1,4-, 1,2- or 2,3-diaminobutane or hexamethylene diamine; and heterocyclic amines such as pyrrolidine, piperidine or morpholine. Ethylene diamine is particularly preferred.

To carry out the transformylation reaction, the amines are preferably used in a quantity which is sufficient to provide about 2 to 25, preferably about 6 to 18 primary and/or secondary amino groups for every N-formyl group.

The transformylation reaction is preferably carried out in the absence of pressure under reflux conditions, more preferably in the absence of a solvent and at a temperature of about 80° to 150° C., most preferably at a temperature of about 90° to 130° C., using amines having corresponding boiling ranges. The reaction is generally complete after 1 to 5 hours. The reaction mixture is then worked up by distillation, for example by thin-layer distillation, such that the end products of the process are obtained as the distillation residue. It is readily possible in accordance with this process to obtain products containing only small residues of N-formyl groups. In addition, the concentration of these N-formyl groups may be minimized by using a large excess of amine within the ranges mentioned in the transformylation reaction. However, it is also possible, for the purpose of minimizing the residual content of N-formyl groups in the distillation residue, to react the distillation residue again with an amine in a second transformylation reaction and then work up the reaction mixture obtained.

Isocyanurate polyisocyanate mixtures containing
a) about 40 to 90% by weight of N,N',N"-tris-(6-isocyanatohexyl)-isocyanurate and
b) about 10 to 60% by weight of higher homologs of this triisocyanate are particularly preferred starting materials for the process according to the invention. When these mixtures are used as starting materials, isocyanurate polyamines are obtained as end products which correspond in their homolog distribution to the polyisocyanate mixtures used as starting material.

Accordingly, these polyamine mixtures according to the invention contain
a) N,N',N"-tris-(6-aminohexyl)-isocyanurate and
b) higher homologs of this triamine containing more than one isocyanurate ring.

It may roughly be assumed that about 40 to 90% by weight of component a) and about 10 to 60% by weight of component b) are present in the mixture, based on the total weight of components a) and b).

The homolog distribution in the particularly preferred starting materials according to the invention and in the polyamine mixtures according to the invention may be determined by gel chromatography. These polyamine mixtures according to the invention have an amine nitrogen content (expressed as N, atomic weight 14) of 6 to 9% by weight.

The polyamine mixtures according to the invention are valuable hardeners for polymer precursors containing epoxide groups and, in particular, isocyanate groups.

Suitable polymer precursors containing epoxide groups which may be hardened with the polyamines according to the invention include any organic epoxy resins of the type described, for example, in Ullmann's Encyclopedia of Industrial Chemistry, 5th Edition, Vol. A 9,547-563, VCH Verlags Gesellschaft, Weinheim (1987) and used, for example, as adhesives or coating compositions.

The polymer precursors containing isocyanate groups which may be hardened with the polyamine mixtures according to the invention include in particular the known NCO prepolymers mentioned as suitable starting materials for the process according to the invention in 3. above and also NCO prepolymers obtained by the reaction of excess quantities of the diisocyanates mentioned by way of example with mixtures of organic polyhydroxyl compounds and monohydric alcohols. NCO prepolymers such as these may be used, for example, for the production of aqueous polyurethane dispersions, as described hereinafter in Example 3.

In the following examples, all percentages are by weight unless otherwise indicated.

EXAMPLE 1 a) Formylation of a polyisocyanate mixture 92.2 g anhydrous formic acid were added dropwise at 50° C. to 400 g of a commercially available trimer of hexamethylene diisocyanate containing 51% N,N',N"-tris-(isocyanatohexyl)-isocyanurate and 49% higher homologs of this triisocyanate (NCO content of the polyisocyanate mixture: 21.5%, viscosity at 24° C.: 3,500 mPa.s) at a rate such that the temperature of the reaction mixture rose to 80° C. The completion of the formylation reaction was determined by the end of the evolution of $CO_2$ and by the absence of the NCO band (IR). 405 g of the N-formylated intermediate product corresponding to the starting mixture were obtained in the form of a wax-like colorless substance.

| Analysis (%) | C | H | N |
|---|---|---|---|
| | 56.8 | 8.0 | 16.5 |

Nuclear resonance spectrum:
$^1$H-NMR (200 MHz, DMSO) δ

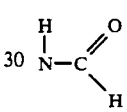

(broad 7.8 to 8); CH$_2$ (broad 3.7);

CH$_2$ (broad 3.1); CH$_2$ (broad 1.1 to 1.7) (ratios: 1:1:1:4).

b) Preparation of a polyamine mixture 500 g of 18.5% aqueous hydrochloric acid were added to the N-formylated intermediate product of Example 1a) and the resulting mixture was subjected to acidic hydrolysis for 1 hour under reflux conditions. Volatile constituents were then separated under vacuum and the colorless amine hydrochloride obtained was dissolved in 100 g water. 300 g of 45% sodium hydroxide were then added dropwise with vigorous stirring and cooling with ice water over a period of 30 minutes at 0° to 20° C. 400 g of a 1:1 isopropanol/toluene mixture were added to the amine/salt mixture during addition of the sodium hydroxide and the reaction mixture was stirred for 1 hour at room temperature. The upper phase was separated, dried with sodium sulfate, filtered and freed under vacuum from low-boiling constituents (50° C., 0.1 mbar). 320 g of a colorless polyamine mixture having an amine nitrogen content of 7.5% were obtained. The molar homolog distribution of the polyamine mixture corresponded to the polyisocyanate mixture used as starting material.

| Analysis (%) | | |
|---|---|---|
| C | H | N |
| 58.5 | 9.4 | 18.7 |

Nuclear resonance spectrum:
$^1$H-NMR (200 MHz, DMSO) δ
CH$_2$ (broad 3.8); CH$_2$ (2.5); CH$_2$ and NH$_2$ (broadened multiplet 1.1 to 1.7) (ratio 1:1:5).

EXAMPLE 2 a) Formylation of a polyisocyanate mixture 200 g of a polyisocyanate mixture having an NCO content of 23.6% and a viscosity at 24° C. of 1,000 mPa.s., prepared by the partial trimerization of hexamethylene diisocyanate and containing a) 70% of the corresponding triisocyanate and b) 30% of higher homologs were formylated with 52 g anhydrous formic acid at 50° to 80° C. as described in Example 1a). The colorless isocyanate-N-formyl mixture obtained was immediately subjected to acidic hydrolysis.

b) Preparation of a polyamine mixture 250 g of 44% aqueous methane sulfonic acid were added to the formylated intermediate product of Example 2a) and the resulting mixture was subjected to acidic hydrolysis for 1 h under reflux conditions. Volatile constituents were then removed under vacuum and the salt residue was dissolved in 100 g water. 60 g sodium hydroxide were then added in portions at 0° to 20° C. while stirring and cooling with ice. The amine/salt mixture formed was thoroughly stirred with 250 g 1-butanol. Working up in accordance with Example 1b) provided 170 g of a colorless polyamine mixture which had an amine nitrogen content of 8.0% and a molar homolog distribution which corresponded to the molar homolog distribution of the starting isocyanate.

EXAMPLE 3 (Application Example)

a) Preparation of an NCO prepolymer

A mixture of 289 g (0.17 moles) of a polyester diol (molecular weight 1,700) prepared from adipic acid and a mixture of 1,6-dihydroxyhexane and neopentyl glucol in a weight ratio of 1.9:1 and 4.2 g of a monohydric polyether alcohol (molecular weight 2,150) prepared by the alkoxylation of n-butanol using a mixture of ethylene oxide and propylene oxide in a molar ratio of 80:20 as the alkoxylating agent were dehydrated under vacuum at 100° C. 56.6 g (0.337 moles) 1,6-diisocyanatohexane were added to this mixture at 60° C. The reaction mixture was then heated with stirring to 105° C. and the mixture was kept at this temperature for 2 h. After cooling to 60° C., the reaction mixture was dissolved in 150 g acetone. The NCO content, based on solids, was 3.74%.

b) Preparation of a crosslinked polyurethane urea dispersion 500 g of the prepolymer solution of Example 3a) were diluted with 710 ml acetone, followed by the addition with stirring at 40° C. of a mixture of 3 g isophoronediamine, 3 g hydrazine and 8.7 g of the sodium salt of N-(2-aminoethyl)-2-aminoethane sulfonic acid dissolved in 40 ml water. After 5 minutes, 5.7 g of the polyamine mixture of Example 1b) were added with thorough stirring. After another 10 minutes, the product was dispersed with 875 ml distilled water at 45° C. and the acetone was distilled off under vacuum.

A stable aqueous polyurethane urea dispersion having the following characteristic data was obtained:

| | |
|---|---|
| Solids content: | 30% |
| pH value: | 6.5 |
| Urea groups: | 4.4% |
| Sulfonate groups: | 1.0% |
| Solvent: | none. |

A film cast from the dispersion was dried first in air (overnight) and then for 30 minutes at 130° C. The tack-free optically clear, high-gloss film obtained had excellent adhesion to glass and aluminium.

EXAMPLE 4 (Application)

Example 3 was repeated using 4.5 g of the polyamine mixture of Example 2b). A stable, crosslinked, aqueous polyurethane urea dispersion having a solids content of 32.5% and a pH value of 7.3 was obtained.

The dispersion was insoluble in dimethyl formamide at both room temperature and at 70° C., demonstrating that the polyurethane was crosslinked. The dispersion was suitable for coating leather or paper.

EXAMPLE 5 (Application)

2.4 g of a commercially available epoxy resin (Uhu 300 Binder, a product of the Uhu Company, D 7580 Bühl) were thoroughly mixed with 2.45 g of the polyamine mixture of Example 1b). The mixture was fully cured after 30 minutes at 100° C. A film prepared from the two-component adhesive was scratch-resistant, colorless and slightly opaque. Adhesion to wood, glass and aluminum was excellent.

EXAMPLE 6 (Application)

2.4 g of the epoxy resin described in Example 5 were mixed with 2.35 g of the polyamine mixture of Example 2b). the reaction mixture obtained was suitable as an adhesive for glass plates. After hardening at 80° C., glass specimen holders bonded crosswise could not be separated without breaking.

EXAMPLE 7 a) Formylation of a polyisocyanate mixture 100 g anhydrous formic acid were added dropwise at 50° C. to a mixture of 400 g of the hexamethylene diisocyanate trimer described in Example 1a) and 50 g toluene at a rate such that the temperature of the reaction mixture rose to 70° C. The completion of the formylation reaction was indicated by the end of the evolution of $CO_2$ and by the absence of the NCO band (IR). After separation of the low-boiling constituents under vacuum, 406 g of the N-formylated intermediate product which corresponded in its molar homolog distribution to the starting mixture were obtained in the form of a wax-like, colorless substance.

| Analysis % | C | H | N |
|---|---|---|---|
| | 56.9 | 8.0 | 16.6 |

Nuclear resonance spectrum:

$^1$H-NMR (200 MHz, DMSO) δ:

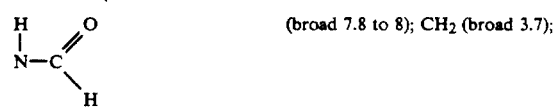

(broad 7.8 to 8); CH$_2$ (broad 3.7);

CH$_2$ (broad 3.1); CH$_2$ (broad 1.1 to 1.7) (ratios: 1:1:1:4).

b) Preparation of a polyamine mixture

The N-formylated intermediate product of Example 7a) was stirred for 2 hours under reflux conditions (internal temperature 120° C.) in 1000 g ethylene diamine. After separation of the volatile constituents (ethylene diamine and formyl homolog) by thin-layer distillation at 140° C./0.1 mbar, 350 g of a clear, light yellow polyamine mixture having an amine nitrogen content of 7.3% were obtained.

EXAMPLE 8

Example 7a) was repeated. The N-formylated intermediate product obtained was stirred for 1 hour under reflux conditions in 500 g ethylene diamine, freed from volatile constituents by thin-layer distillation as in Example 7 and the resulting bottoms product stirred for 1 hour under reflux conditions in 240 g ethylene diamine. Working up as in Example 7 provided 340 g of a yellow polyamine mixture having an amine nitrogen content of 7.2%.

EXAMPLE 9 a) Production of an NCO prepolymer 3024 g 1,6-diisocyanatohexane were added at 60° C. to 1680 g of a dehydrated polyether diol, OH value 200, prepared by the prepoxylation of bisphenol A. The mixture was then stirred at 100° C. until the NCO content had reached 26.7% (3 hours). After separation of excess 1,6-diisocyanatohexane by thin-layer distillation (150° C./0.1 mbar), 2600 g of an NCO prepolymer having an NCO content of 8% were obtained.

b) Formylation and subsequent transformylation 83 g anhydrous formic acid were added dropwise at 50° C. to a mixture of 890 g of the prepolymer of Example 3a) and 50 g toluene at a rate such that the temperature rose to 70° C. After the formylation reaction, low-boiling constituents were removed under vacuum, the residue was dissolved in 816 g ethylene diamine and the resulting solution was stirred for 1 hour under reflux conditions (120° C.). Working up as in Example 7 provided a colorless, highly viscous polyamine mixture having an amine nitrogen content of 2.7%.

EXAMPLE 10 (Use Example)

a) Preparation of an NCO prepolymer

The mixture of 289 g (0.17 moles) of the polyester diol described in Example 3a) and 4.2 g of a monohydric polyether alcohol described in Example 3a) was dehydrated under vacuum at 100° C., followed by the addition at 60° C. of 56.6 g (0.337 moles) 1,6-diisocyanatohexane. The mixture was then heated with stirring to 105° C. and kept at that temperature for 2 hours. After cooling to 60° C., the mixture was dissolved in 150 g acetone. The NCO content, based on solids, was 3.2%.

b) Preparation of a crosslinked polyurethane urea dispersion 400 g of the prepolymer solution of Example 10a) were diluted with 710 ml acetone, followed by the addition with stirring at 40° C. of a mixture of 1.3 g isophorone diamine, 1.0 g hydrazine and 10.0 g of the sodium salt of N-(2-aminoethyl)-2-aminoethane sulfonic acid dissolved in 40 ml water. After 5 minutes, 5.1 g of the polyamine mixture of Example 7b) according to the invention was added with thorough stirring. After another 10 minutes, the mixture was dispersed with 875 ml distilled water at 45° C. and the acetone was distilled off under vacuum.

A stable, aqueous polyurethane urea dispersion having the following characteristic data was obtained:

| | |
|---|---|
| Solids content: | 30.2% |
| pH value: | 7.0 |
| Urea groups: | 3.8% |
| Sulfonate groups: | 1.0% |
| Solvent: | none |

A film cast from the dispersion was dried first in air (overnight) and then for 30 minutes at 130° C. A tack-free, optically clear, glossy film with excellent adhesion to glass and aluminum was obtained.

EXAMPLE 11

Example 10b) was repeated using 0.6 g diethylene triamine, 0.9 g hydrazine hydrate and 20.9 g of the polyamine mixture of Example 9b) according to the invention.

A stable, crosslinked, aqueous polyurethane urea dispersion having a solids content of 32.1% for a pH value of 7.0 was obtained. The dispersion and a coating formed therefrom were both insoluble in dimethyl formamide.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of a compound containing one or more aliphatically or cycloaliphatically bound primary amino groups which comprises reacting an organic compound containing one or more aliphatically or cycloaliphatically bound isocyanate groups with formic acid to convert the isocyanate groups to N-formyl groups and subsequently converting said N-formyl groups to amino groups in a transformylation reaction.

2. The process of claim 1 wherein said organic isocyanate comprises an organic polyisocyanate containing at least two aliphatically and/or cycloaliphatically bound isocyanate groups.

3. The process of claim 1 wherein said organic isocyanate comprises
   a) about 40 to 90% by weight, based on the total weight of components a) and b), of N,N',N''-tris-(6-isocyanatohexyl)isocyanurate and
   b) about 10 to 60% by weight, based on the total weight of components a) and b), of higher homologs of the isocyanurate of component a) containing more than one ixocyanurate ring.

4. The process of claim 1 which comprises conducting said transformylation reaction by reacting said N-formyl groups with a primary or secondary amine having a boiling point of about 80 to 150° C. at 1013 mbar.

5. The process of claim 2 which comprises conducting said transformylation reaction by reacting said N-formyl groups with a primary or secondary amine having a boiling point of about 80° to 150° C. at 1013 mbar.

6. The process of claim 3 which comprises conducting said transformylation reaction by reacting said N- formyl groups with a primary or secondary amine having a boiling point of about 80° to 150° C. at 1013 mbar.

7. The process of claim 4 wherein said primary or secondary amine comprises ethylene diamine.

8. The process of claim 5 wherein said primary or secondary amine comprises ethylene diamine.

9. The process of claim 6 wherein said primary or secondary amine comprises ethylene diamine.

* * * * *